(12) United States Patent
Warkentin et al.

(10) Patent No.: US 9,712,893 B2
(45) Date of Patent: Jul. 18, 2017

(54) SENSING DEVICE AND METHOD TO MONITOR PERISHABLE GOODS

(71) Applicant: Digi International Canada Inc., St. Catharines (CA)

(72) Inventors: Colin Warkentin, St. Catharines, Ontario (CA); Chris DiLalla, St. Catharines, Ontario (CA); Mirek Wojtowicz, Etobicoke, Ontario (CA); Sara Steele, St. Louis Park, MN (US)

(73) Assignee: Digi International Canada Inc., St. Catharines (CA)

( * ) Notice: Subject to any disclaimer, the term of this patent is extended or adjusted under 35 U.S.C. 154(b) by 0 days.

(21) Appl. No.: 14/255,640

(22) Filed: Apr. 17, 2014

(65) Prior Publication Data

US 2014/0313055 A1    Oct. 23, 2014

(30) Foreign Application Priority Data

Apr. 18, 2013   (CA) ..................................... 2813285

(51) Int. Cl.
*G08B 21/00* (2006.01)
*H04Q 9/00* (2006.01)
*G01N 33/02* (2006.01)

(52) U.S. Cl.
CPC ............ *H04Q 9/00* (2013.01); *G01N 33/02* (2013.01); *H04Q 2209/40* (2013.01); *H04Q 2209/43* (2013.01); *H04Q 2209/823* (2013.01); *H04Q 2209/88* (2013.01); *H04Q 2209/883* (2013.01)

(58) Field of Classification Search
None
See application file for complete search history.

(56) References Cited

U.S. PATENT DOCUMENTS

| 5,313,848 A | 5/1994 | Santin et al. |
| 5,920,287 A * | 7/1999 | Belcher ................... G01S 5/021 342/450 |
| 6,285,282 B1 | 9/2001 | Dorenbosch et al. |

(Continued)

OTHER PUBLICATIONS

International Search Report for PCT/CA2014/000354, Date of mailing: Jul. 15, 2014.

(Continued)

*Primary Examiner* — Brian Zimmerman
*Assistant Examiner* — Thomas McCormack
(74) *Attorney, Agent, or Firm* — Hoffmann & Baron, LLP (57) ABSTRACT

A sensing device monitors conditions in a local environment and wirelessly communicates those conditions. The sensing device has a sealed body comprised of a material suitable to contact food and which is cleanable for re-use. The sensing device has a condition sensor, a processor, a memory and a communication device, a motion sensor and an energy source such as a battery carried by the sealed body. The motion sensor detects motion of the sealed body and acts as a switch for the processor. The sensing device may be placed in contact with perishable food products to monitor conditions in the environment around perishable food products. Conditions of the perishable food are monitored by placing a sensor which has been activated by motion in the environment containing perishable food products and detecting, storing and transmitting information collected by the condition sensor to a receiver.

35 Claims, 7 Drawing Sheets

(56) References Cited

U.S. PATENT DOCUMENTS

| | | |
|---|---|---|
| 7,075,442 B2 * | 7/2006 | Lion .................... G01K 1/024 340/540 |
| 7,151,455 B2 | 12/2006 | Lindsay et al. |
| RE40,073 E | 2/2008 | Breed |
| 7,495,558 B2 | 2/2009 | Pope et al. |
| 7,538,672 B2 | 5/2009 | Lockyer et al. |
| 7,592,916 B2 | 9/2009 | Staples |
| 7,784,707 B2 | 8/2010 | Witty et al. |
| 7,808,383 B2 | 10/2010 | Cargonja et al. |
| 7,828,345 B2 | 11/2010 | Terry et al. |
| 7,866,555 B2 | 1/2011 | Schmid et al. |
| 7,937,244 B2 | 5/2011 | Kadaba |
| 8,047,432 B2 | 11/2011 | Breed |
| 8,223,680 B2 | 7/2012 | Twitchell, Jr. |
| 2002/0069028 A1 | 6/2002 | Merz et al. |
| 2003/0163287 A1 | 8/2003 | Vock et al. |
| 2004/0100379 A1 | 5/2004 | Boman et al. |
| 2007/0050271 A1 | 3/2007 | Ufford et al. |
| 2007/0124020 A1 | 5/2007 | Staples |
| 2007/0171076 A1 | 7/2007 | Stevens et al. |
| 2007/0247306 A1 | 10/2007 | Case, Jr. |
| 2008/0129448 A1 * | 6/2008 | Reichling ............. G08C 17/02 340/5.72 |
| 2010/0100327 A1 * | 4/2010 | Jensen .................. G01D 9/005 702/2 |
| 2011/0029413 A1 | 2/2011 | Ben-Tzur et al. |
| 2011/0193710 A1 * | 8/2011 | McIlvain ................. B60P 3/20 340/585 |
| 2012/0111044 A1 | 5/2012 | Chen et al. |
| 2012/0252488 A1 | 10/2012 | Hartmann et al. |
| 2012/0274470 A1 * | 11/2012 | Sandvick ............... G01N 33/02 340/584 |

OTHER PUBLICATIONS

International Preliminary Report on Patentability for PCT/CA2014/000354, Corrected Version dated Aug. 6, 2015, Date of Completion of Report: Jul. 31, 2015.

International Preliminary Report on Patentability for PCT/CA2014/000354, Corrected Version dated Sep. 9, 2015, Date of Completion of Report: Jul. 31, 2015.

Written Opinion of the International Searching Authority for PCT/CA2014/000354, Date of mailing: Jul. 15, 2014.

* cited by examiner

SENSING DEVICE AND METHOD TO MONITOR PERISHABLE GOODS

CROSS-REFERENCE TO RELATED APPLICATION

This application claims the benefit of Canadian Patent Application No. 2,813,285, filed Apr. 18, 2013, the entire contents of which are incorporated by reference herein.

FIELD OF THE INVENTION

The present invention relates generally to a sensing device and more particularly to a sensing device for detecting a condition in an environment around perishable items, such as food.

BACKGROUND OF THE INVENTION

Proper perishable food management requires those involved in transporting, storing or preparing food to appropriately monitor and keep records of conditions in which food is kept. Food safety regulations, such as HACCP and FDA Food Safety Modernization Act (FSMA), require the implementation of certain procedures and monitoring protocols for managing perishable food safety and quality. Perishable goods include but are not limited to perishable foods such as fresh or frozen meats, vegetables, fruits, breads, milk and milk products such as cheese and the like.

Such perishable food is often transported and stored in environments where certain conditions need to be controlled. For example, perishable food items may need to be refrigerated or frozen in order to maintain freshness. If food is not stored in an environment under the proper conditions, the food may spoil immediately or before its expected expiry date. It is important for the owners of perishable goods to be able to track the conditions in the environments where those goods are stored. It is also important for purchasers of perishable goods to know that such purchased goods have been kept in the proper conditions.

For example, it is common for perishable foods to be transported in refrigerated vehicles. The foods may be shipped from a warehouse and transported in a refrigerated trailer. In many cases, there is no oversight provided to ensure that the food was kept at the proper temperature for the duration of the trip. In many cases, a driver will sign a form at the conclusion of the trip that in an effort to verify the food was maintained in proper conditions. It may be impossible to independently confirm whether the driver left the trailer door open or whether the refrigeration unit temporarily failed at some point during the journey.

Another situation where it is important to track environmental conditions is in freezers and refrigerators in restaurants and grocery stores. Restaurants often have walk-in freezer and/or refrigeration units that require temperature regulation. Grocery stores will have multiple freezer and refrigeration units for displaying food for sale. It is very important to keep the temperatures of these freezer or refrigerator units at a certain level to ensure that the food does not spoil. The temperature within a freezer unit may need to be checked and logged frequently, in some cases more than once a day. In some cases, a person may need to physically enter the freezer or refrigerator to check the temperature in the unit and then enter the measured temperature into a log. Physically entering the freezer unit is undesirable because it causes loss of heat from the freezer and may increase the risk that the door is accidentally left open, thereby causing the food to spoil. It may be difficult to track temperatures in freezer units at restaurants because it is common for regulations to require that any items that are placed inside a restaurant refrigerator or freezer must be made from a food-grade material requiring special thermometers.

Furthermore, freezers will often have a defrost cycle, during which the temperature within the unit may increase. The operation of the defrost cycle may prevent the use of a simple temperature switch. A temperature switch would cause an alarm condition when the temperature in the freezer rose above a set level. However, the temperature switch would identify false alarms during a defrost cycle. On the other hand, a sensor that is programmed to ignore a defrost cycle may also be ineffective, because a freezer unit can fail after the defrost cycle is completed, at which point the unit fails to turn back.

Another issue that exists in dealing with technology for sensing conditions in environments with low temperatures is that often batteries are less effective in cold conditions. For example, although lithium batteries may operate to below minus 40 degrees Celsius, the battery capacity may be reduced by more than half at those temperatures. For portable temperature sensors to be effective, it is important to have a long battery life. On the other hand, high powered batteries may be undesirably heavy and bulky. Furthermore, active radio transmitters on portable sensors require an energy source, unlike traditional passive RFID tags. Many portable sensors with active radio transmitters may have prohibitively short battery lives when used in applications where the sensors are exposed to in cold conditions.

Some portable sensor systems induce a sleep function during which the sensor is dormant. For example, U.S. Pat. No. 7,495,558 to Pope et al. ("Pope") describes an RF label that may be applied to a packaged product to track its shelf life. In some embodiments, the system has a power management module that periodically wakes up a freshness monitoring component from a sleep or other low power state to gather the sensor measurements. The system is connected to an individual packaged item and tracks freshness at set intervals.

The system in Pope tracks freshness at set timed intervals. However, product freshness may be heavily impacted during a change of state of the environment surrounding the product, such as when the product is moved between two separate environments or where a refrigerator is opened. For example, if a product is unloaded from a transportation trailer and placed outside on a hot day before ultimately being loaded into a restaurant freezer, a timed sensor may not take a reading during the short time in which the product is left outside. However, the packaged product may spoil quite rapidly in hot conditions, which may not be detected by the system in Pope.

Furthermore, the Pope system is described as being placed on the outside packaging for items such as wine or pharmaceuticals, where sterilization and food safety are not a concern. Food distribution and retailing is typically a high volume and low margin activity. As such new technologies, which typically are expensive, are not readily adapted into the food industry due to cost concerns. Thus, any solutions in the food industry have to be very cost effective. Individual sensors for each package of product can be very expensive, and may make the technology uneconomic.

Other patents and patent applications of general interest in the field of portable sensors include:

U.S. Pat. Nos. 5,313,848, 6,285,282, 7,151,455, 7,495,558, 7,538,672, 7,592,916, 7,784,707, 7,808,383, 7,828,345, 7,866,555, 7,937,244, 8,047,432, 8,223,680, RE 40,073; and U.S. Patent Application Publication Nos. 2003/0163287, 2004/0100379 2007/0171076, 2011/0029413, 2012/0111044, 2012/0252488.

Therefore there is a continuing need for a sensing device that is portable, has a long battery life, is suitable for contacting food items and allows for efficient tracking of important events during the operation of the device. Further such a device needs to be cost effective and useful in respect of a wide variety of perishable items.

SUMMARY OF THE INVENTION

The present invention is directed to an improved sensing device that monitors conditions in a local environment containing, for example, perishable products and which sensing device is responsive to motion. Preferably, the sensing device is cleanable for re-use and can communicate using a wireless communicator. Most preferably the sensing device need not be placed on every package, but can be placed in a pallet or other large volume of perishable food so as to be cost effective.

According to preferred embodiments of the present invention there is provided a sensing device for monitoring conditions in a local environment containing perishable goods and wirelessly communicating said monitored conditions. The sensing device preferably has a sealed body comprised of a material suitable to contact food and which is cleanable for re-use. A low-energy wireless communicator may be contained within said sealed body, and a condition sensor is carried by said sealed body. A processor is operatively connected to the temperature sensor and the wireless communicator. The processor is also preferably contained in said sealed body. An energy source is operatively connected to the processor to supply power. A motion sensor is operatively connected to the processor for detecting motion of said sealed body. The motion sensor acts as a switch for said processor. The device may be placed in contact with perishable food products to monitor conditions affecting said perishable food products and communicate the monitored conditions by means of said wireless communicator.

According to another embodiment of the present invention, there is provided a method of monitoring a condition of perishable food products using a sensing device. The sensing device comprises a sealed body comprised of a material suitable to contact food and which is cleanable to food safety standards for re-use. A low-energy wireless communicator is contained within said sealed body. A condition sensor is contained in said sealed body. A processor is operatively connected to the condition sensor and the wireless communicator. The processor is contained in said sealed body. An energy source is operatively connected to the processor to supply power. A motion sensor is operatively connected to the processor for detecting motion of said sealed body. A sensing device is provided which is placed in an environment containing the perishable food products, in which the sensing device is activated by inducing motion to be detected by the motion sensor. The condition sensor detects a condition in the environment. The sensing device stores the detected condition in the environment in the form of stored condition data. The low-energy communicator transmits the stored condition data to a receiver.

According to another embodiment of the present invention, there is provided a system for monitoring a condition of perishable food products. There is at least one sensing device. The at least one sensing device has a sealed body comprised of a material suitable to contact food and which is cleanable for re-use, a low-energy wireless communicator contained within said sealed body, a condition sensor contained within said sealed body and a processor operatively connected to the condition sensor and the wireless communicator, an energy source operatively connected to the processor to supply power and a motion sensor operatively connected to the processor for detecting motion of said sealed body, to act as a switch for said process. The processor is contained in said sealed body. A hand-held mobile device having a wireless communicator communicates with the low-energy wireless communicator of the sensing device.

According to another embodiment of the invention, there is provided a sensing device for monitoring conditions in a local environment containing perishable goods and wirelessly communicating said monitored conditions. The sensing device comprising a sealed body comprised of a material suitable to contact food and which is cleanable for re-use. The sealed body has a wedge end, a low-energy wireless communicator contained within said sealed body, and a condition sensor carried by said sealed body and situated within the wedge end of the sealed body. A processor is operatively connected to the condition sensor and the wireless communicator. The processor is contained in said sealed body. An energy source is operatively connected to the processor to supply power. The wedge end of the sensing device may be placed in the local environment containing perishable food products to monitor conditions affecting said perishable food products and communicate the monitored conditions by means of said wireless communicator.

BRIEF DESCRIPTION OF THE DRAWINGS

Reference will now be made to the preferred embodiments of the present invention with reference, by way of example only, to the following drawings in which.

DETAILED DESCRIPTION OF THE INVENTION

The present invention is described in more detail with reference to exemplary embodiments thereof as shown in the appended drawings. While the present invention is described below including preferred embodiments, it should be understood that the present invention is not limited thereto. Those of ordinary skill in the art having access to the teachings herein will recognize additional implementations, modifications, and embodiments which are within the scope of the present invention as disclosed and claimed herein. For the purposes of clarity, not every component is labeled in every figure, nor is every component of each embodiment of the invention shown where illustration is not necessary to allow those of ordinary skill in the art to understand the invention.

Figure 1:
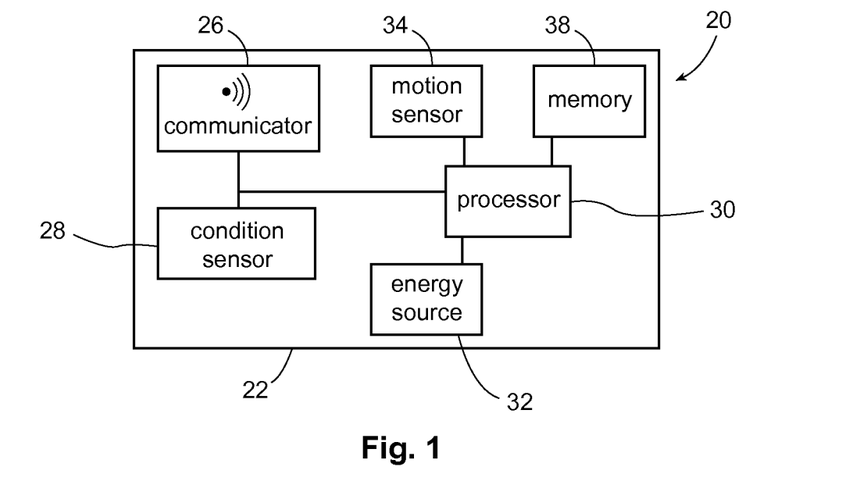
FIG. 1 is a plan diagram of an embodiment of a sensing device.

FIG. 1 shows a sensing device 20 contained within a sealed body 22. The sealed body 22 is made with a material suitable to contact food and which is cleanable for re-use. For example, the sealed body 22 may be made from a material such as plastic, which is easily molded and can be formed into a cleanable package or stainless steel. Most preferably the body material would be of the type approved for food equipment materials by NSF International (formerly National Sanitization Organization). Preferably, the sealed body 22 is comprised of a food-grade material and is configured to be easily sanitized to food grade standards. The sealed body 22 is preferably waterproof and has no external buttons to ensure it is easily cleanable. The sealed nature of the sealed body 22 also ensures that it is tamper-proof.

A low-energy wireless communicator 26 is contained within said sealed body. Preferably, the low-energy wireless communicator 28 is a Bluetooth™ low-energy (BLE) protocol radio module. A condition sensor 28 is carried by said sealed body 22. A processor 30 is operatively connected to the condition sensor 28 and the wireless communicator 26. The processor 30 is also contained in the sealed body 22. An energy source 32 is shown operatively connected to the processor to supply power. In this embodiment, the energy source 32 is a type of battery that provides power at the typical temperature range used in food preservation. Good results have been achieved with a lithium based battery within the sealed body 22. For example, the lithium battery may be a 3.3 V lithium battery. Preferably, the battery may provide power for at least a year or more under the use conditions described below. In some cases the battery may be made rechargeable, such as with an induction charger that does not require the body to be opened or even any external contacts. Other energy sources are also possible as long as the sealed body 22 remains cleanable for re-use. A motion sensor 34 is operatively connected to the processor. Preferably, the motion sensor 34 is a MEMS device such as a 3-axis accelerometer, but it is contemplated that the present invention may include any other device that is capable of detecting motion of the sealed body 22 such as any other accelerometer, gyroscope or a compass.

Preferably, a memory 38 is operatively connected to the condition sensor 28 to store monitored conditions obtained by the condition sensor 28. The memory 38 is contained in the sealed body 22. The memory may be a solid state memory.

The sensing device 20 may be placed in an environment containing perishable products in a variety of different positions. For example, the sensing device 20 may be placed in a free-standing manner in the environment, for example by being placed loosely with a box of food stuff such as produce, fruit or the like. The sensing device 20 may also be affixed to a product such as using cardboard, a paper clip, a hook and loop attachment (Velcro™), magnetic clip, or, adhesive pad to connect it to an item, such as a product box, pallet or structure in the environment where perishable items are being monitored. As discussed in more below detail with reference to FIGS. 10 and 11, it is also possible to partially insert the sensing device 20 into a container such as a cardboard box. It is also possible to secure the sensing device to a pallet or door containing perishable goods to be monitored. An aspect of the present invention is the ability to use one sensing device to track the local conditions around many individual products, thus rendering the present invention cost effective in the high volume low margin food industry.

Figure 9:
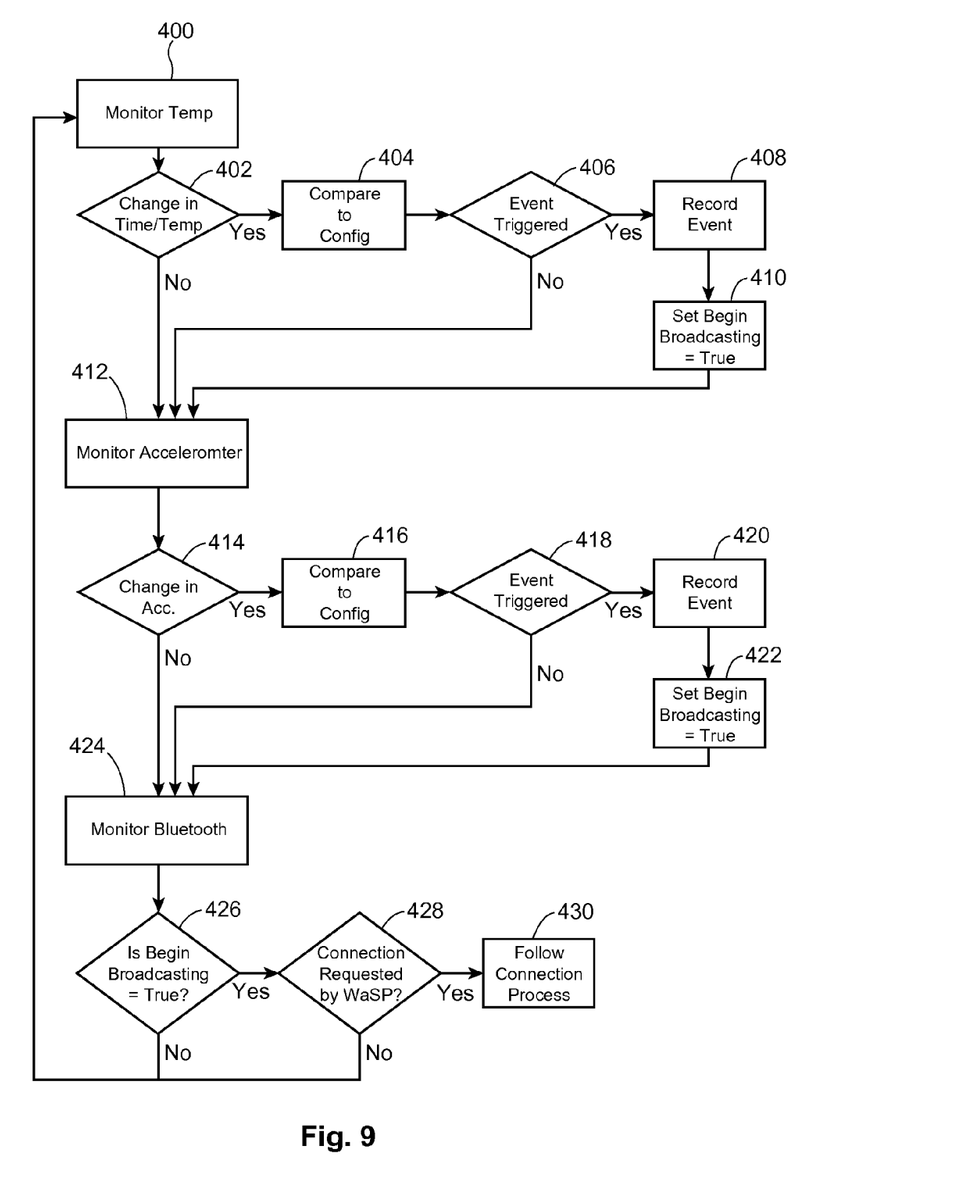
FIG. 9 is a flow diagram describing events which cause a sensing device to activate a broadcast signal.

As is described in more detail in FIG. 9, the motion sensor 34 may act as a switch for said processor. For example, the sensing device may be activated by motion detected by the motion sensor 34. The sensing device 20 may be placed in contact with perishable food products to monitor conditions affecting said perishable food products and communicate the monitored conditions by means of the wireless communicator 26. Where the condition sensor 28 is a temperature sensor, the sensing device 20 may cause the temperature sensor 28 to detect a temperature in an environment in response to a certain type of motion of the sealed body 22 being detected by the motion sensor 34. The condition sensor 28 may also track various conditions other than temperature according to the present invention. For example, the condition sensor 28 may also track the distance travelled by a trailer, if mounted to a door, it can track a door opening and closing history for trailers, coolers or freezers, and other conditions which may be desirable to track such as humidity or exposure to light. The present invention therefore comprehends sensing a broad range of conditions which may pertain to the conditions, over time, to which perishable items such as food products are exposed. Although initially the present invention comprehends only one or two such local conditions to be sensed, the present invention is not limited in this respect and more conditions can be simultaneously sensed provided there is enough battery power and it is cost effective to sense such additional conditions.

The condition sensor 28 detects the conditions of the environment surrounding the sensor, such as the ambient air inside a trailer, the inside of product packaging, the air surrounding a pallet or the air inside a display case, freezer or cooler. The condition sensor may also be part of a sensing network. The sensing device can also be used to determine the proximity of various things such tarps, dollies, forklifts, racks and other items based on the last known communication between the sensing device and another sensing device in the network. For example, if a sensing device is placed on a trailer and another sensing device or gateway or access point is on a transportation vehicle which pulls the trailer, then it is possible to determine the time at which the two devices last communicated, which can be used to determine the location at which the trailer and vehicle were separated.

Figure 2:
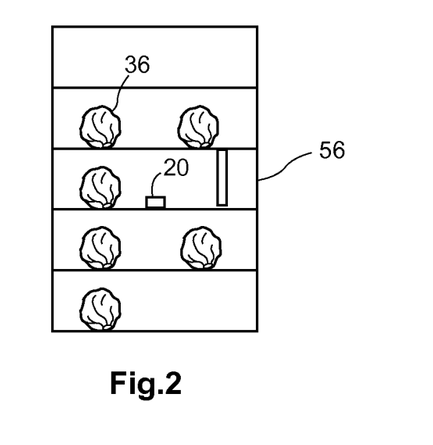
FIG. 2 is a front view of a display case containing the sensing device and perishable foods.

In FIG. 2, the sensing device 20 operates as a temperature sensing device and the condition sensor 28 (FIG. 1) is a temperature sensor. The temperature sensing device 20 is placed in an environment containing perishable food products 36, such as a food retailer display case 56. By placing the sensing device in a display case 56, the need for manually checking cooler temperatures multiple times a day is removed. The sensing device 20 can be placed in a variety of locations, depending on what needs to be monitored and where. For example, the sensing device may be mounted inside a walk-in freezer or refrigerator or prep cooler to continuously monitor temperature sensitive inventory. A number of sensing devices 20 may be placed throughout a warehouse to provide real-time monitoring of every temperature zone in the warehouse. The sensing device 20 may also be placed inside a product packaging or pallet to provide precise temperature data history from storage to staging and transportation. The sensing device 20 may be placed in a vehicle cargo area or trailer. The sensing device 20 may be used in any other location where it is desirable to monitor or detect temperature in an environment that contains food or other perishable items.

It is not necessary to have multiple processors within the sensing device 20 to operate each of the wireless communicator 26 and the condition sensor 28 according to the present invention. The BLE-wireless processor may have integrated code for condition recording and power savings code, as well as code for activating the low-energy wireless communicator 26. The integration of processing onto the BLE module's processor reduces power consumption and cost. In this way, the memory 38 and the processor 30 may be integrated into an internal processor of the BLE protocol radio module. In a preferred embodiment, the processor may be able to operate at less than 8 micro amps.

Figure 3:
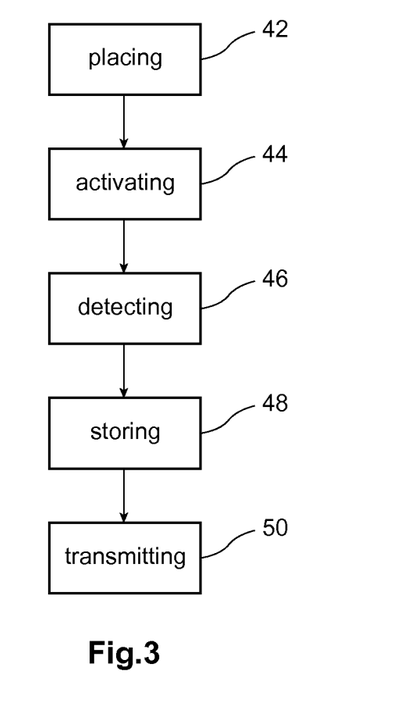
FIG. 3 is a flow diagram of a method of monitoring a condition of perishable food products.

As shown in FIG. 3, a method of monitoring a condition of perishable food products using the sensing device 20 is described. The sensing device is placed 42 in an environment containing the perishable food products, such as the display case 56 (FIG. 2) or other environment. The sensing device is activated 44 by inducing motion to be detected by the motion sensor. For example, as discussed in FIG. 5, the sensing device 20 may be activated by being doubled-tapped. It is not important to the operation of this method the order in which the sensing device 20 is placed or activated in the environment. The sensing device 20 can be activated prior to being placed in an environment or may be placed in an environment then activated. A condition in the environment is detected 46 using the condition sensor 28. The detected condition in the environment is stored 48 on the sensing device in the form of stored condition data. The stored condition data is transmitted 50 to a receiver using the low-energy wireless communicator. The transmission of the stored condition data to a receiver may comprise uploading the stored condition data to a server, or a gateway or access point.

The processor may trigger the condition sensor to detect the condition in the environment after motion is detected by the accelerometer or at set time intervals as determined by the processor. The processor may trigger the condition sensor to detect the condition in the environment both when motion is detected and at set intervals. As will be appreciated by those skilled in the art, the processor is programmable and different time sequences or trigger events may be appropriate for different end use applications. However, the present invention comprehends all such uses.

The sensing device may be configured to update temperature information in real-time. In that case, all of the steps of detecting 46 the condition in the environment, storing 48 the detected condition and transmitting 50 the stored condition data are done in real-time. The storage of the condition data may be stored only long enough to send the data and may not be stored more than instantaneously on the memory. Real-time condition data can sent from the sensing device 20 through the wireless communicator 26 to a wireless device that either activates an alert or connects to a separate processing location that activates an alert. The system may issue alerts to a user through a variety of ways such as email, text or Twitter™ to ensure that the user is aware of the alarm condition and the severity of that condition.

The sensing device 20 may be configured to collect a variety of data points before transmitting the stored data to a receiver, gateway or access point. For example, if the sensing device 20 is placed on a truck trailer, the sensing device 20 may not be in communication with a receiver until it arrives at its ultimate destination. It is important to store detected conditions on the sensing device 20 for the duration of the trip especially if the sensor is out of communication during such trip with any receiver. In situations where condition information is stored in between transmissions, the steps of detecting 46 the condition in the environment and storing 48 the detected condition may be repeated multiple times before the occurrence of the step of transmitting 50 the stored condition data.

As described in more detail in FIG. 9, the processor 30 may be configured to transmit data to a receiver, gateway or access point in response to either the occurrence of a condition detected by the condition sensor 28 or the occurrence of motion detected by the motion detector 34. The processor 30 may store a configuration record correlating threshold conditions to an occurrence of a plurality of events. The processor may monitor one or both of the condition in the environment using the condition sensor and the motion detected by the motion sensor. The occurrence of an event is recorded when one of the conditions in the environment and the motion detected by the motion sensor correlates to an event in the plurality of events.

Figures 4, 5:
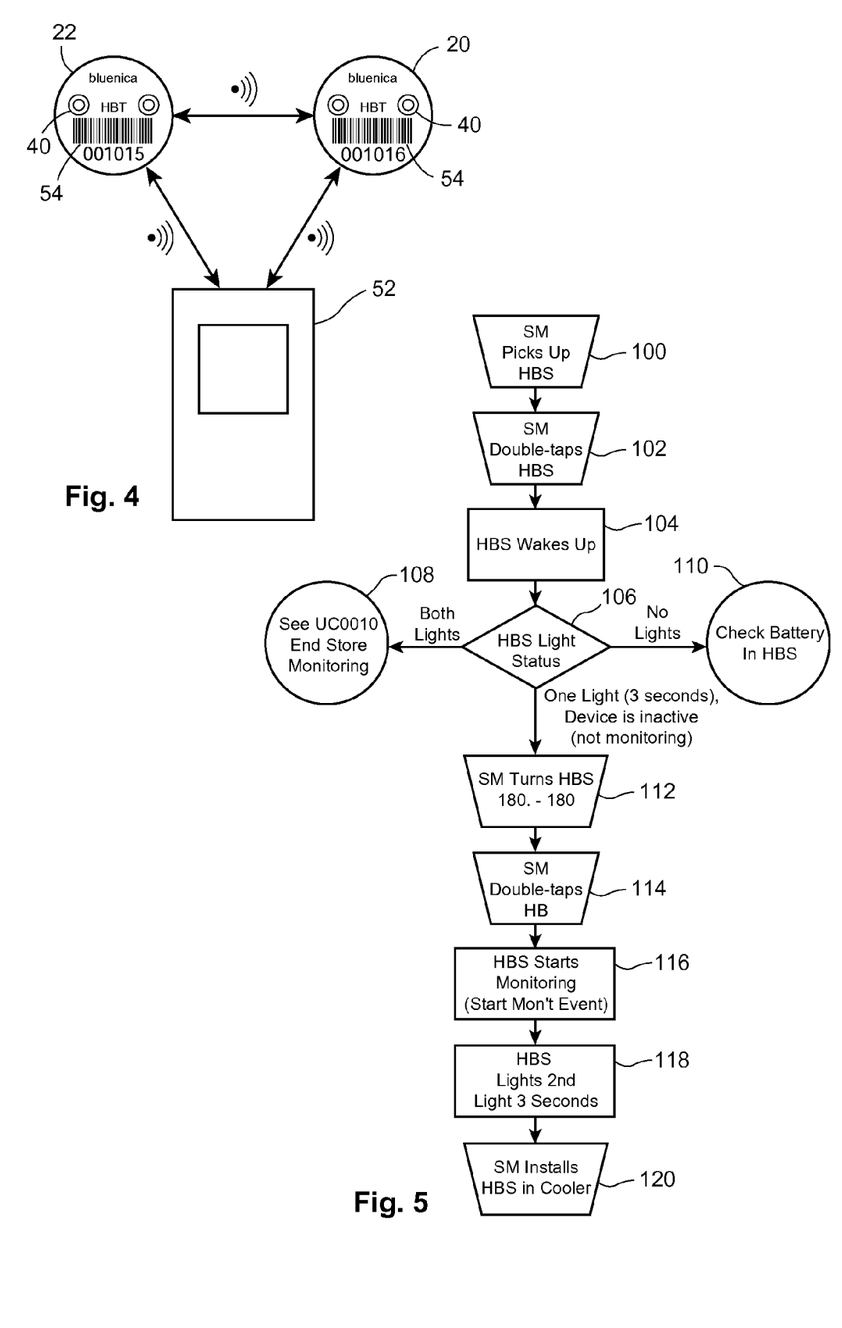
FIG. 4 is a top view of an embodiment of two sensing devices having status lights and a mobile device.
FIG. 5 is a flow diagram describing a method of initiating monitoring of a sensing device.

As shown in FIG. 4, the sensing device 20 has a status display interface on the sealed body 22. The status display interface is shown as two status lights 40. The status display interface 40 is connected to the processor 30 which indicates a current status of the sensing device 20. Other status display interfaces, such as screens may be used as long as the status display interface is not a disproportionate drain on the battery 32. As shown in FIG. 4, the sensing device may be pocket sized. The sensing device 20 has a unique label on it, such as a barcode 54. Other unique labels, such as a matrix bar code or an identifying chip could be used without departing from the scope of the present invention.

A hand-held mobile device 52 having a wireless communicator is shown which is capable of communicating with the low-energy wireless communicator 26 of the sensing device thereby forming a system for monitoring a condition of perishable food products. The mobile device 52 and the wireless communicator 26 may both communicate through Bluetooth™ low-energy (BLE) protocol. Multiple sensing device 26 may be configured to communicate with each other. For example, a sensing device 20 may be mounted on a door of a walk-in freezer or a vehicle cargo door which may communicate to a second sensing device within the freezer or cargo door, such as on a product package or on a pallet.

Figure 6:
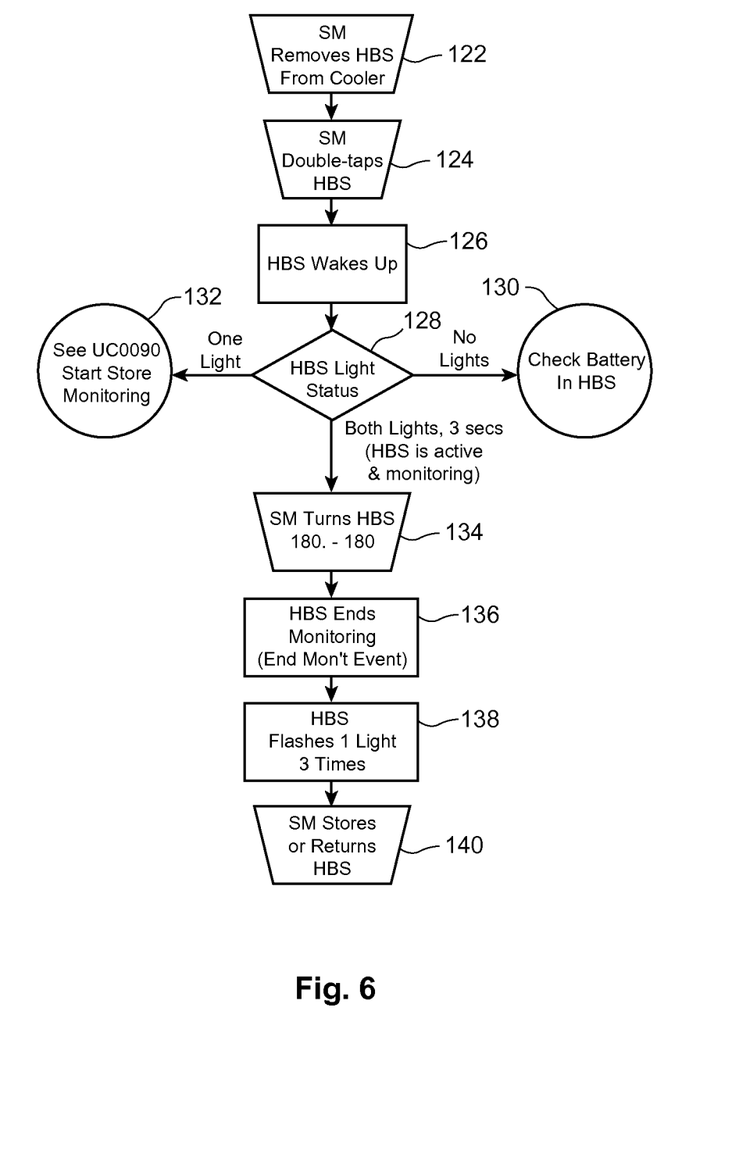
FIG. 6 is a flow diagram describing a method of ending monitoring of a sensing device.

FIGS. 5 and 6 disclose an embodiment of identifying a time period for monitoring when the sensing device 20 (FIG. 1) monitors perishable items in a store environment. In the embodiment, the user is described as a store employee and the environment where conditions are determined is described as a cooler within a store. It will be understood that the methods of activating and deactivating the sensing device may be varied depending on the location being monitored and the condition being monitored. For example, in the case where the location to be monitored is a truck trailer, the time period for monitoring may be initialized in response to the door of the truck trailer opening or closing.

FIG. 5 describes an embodiment of a method of initializing the sensing device 20 (FIG. 1). The employee picks up 100 the sensing device. The employee double taps 102 the sensing device to wake up 104 the sensing device. The sensing device is configured in this embodiment to detect the motion induced when the employee double taps the sealed body 22 (FIG. 1). A status display interface is activated 106 in response to the sensing device waking up. The status display interface is in the form of two status lights 40 (FIG. 4). If both lights turn on after the sensing device wakes up, the sensing device is in a monitoring state and the employee may end 108 the monitoring, if desired. One method of ending store monitoring is described in FIG. 6. If no lights turn on after the sensing device wakes up, the employee will check the battery 110. If one light is on, the device is inactive and not in a monitoring state. To activate the monitoring state, the store monitor can activate the sensing device by inducing an initializing motion on the sensing device. For example, the employee may turn the sensing device by 180 degrees and then rotate the sensing device in the opposite direction by 180 degrees at 112. The sensing device is configured to activate in response to that motion. This specific activation requirement ensures that the sensing device is not activated accidentally if dropped or moved in a manner that is not within the parameters that activate monitoring. The sensing device may be configured to be responsive to various other types of motion in order to active the monitoring. The employee will double tap 114 the sensing device again and sensing device will begin monitoring 116. The status display interface will indicate that the sensing device is active, for example by displaying 118 both status lights for a few seconds. The sensing device is now active and may be placed in an environment such as the cooler where it can begin monitoring 120. It will now be understood that the methods of activation eliminate the need for buttons or the like on the device itself, saving cost and making the device easier to clean and keep clean and sanitized.

FIG. 6 describes an embodiment of a method of ending the time period for monitoring with the sensing device 20 (FIG. 1). The employee removes 122 the sensing device from the cooler and double taps 124 the sensing device. The sensing device wakes up 126 and displays a status on the status lights 128. If there are no lights, the battery is checked 130. If one light is present, then the sensing device is not monitoring 132 and it can be set to monitor by following the method set out in FIG. 5. If both lights are on, the sensing device is active and monitoring and the employee can turn 134 the sensing device by 180 degrees in one direction then 180 degrees in the opposite direction to mark an end to the time period for monitoring 136. The sensing device will display one status light 138 for a few seconds and the store monitor may store or return the sensing device to a storage location or move to a separate location 140.

Figure 7:
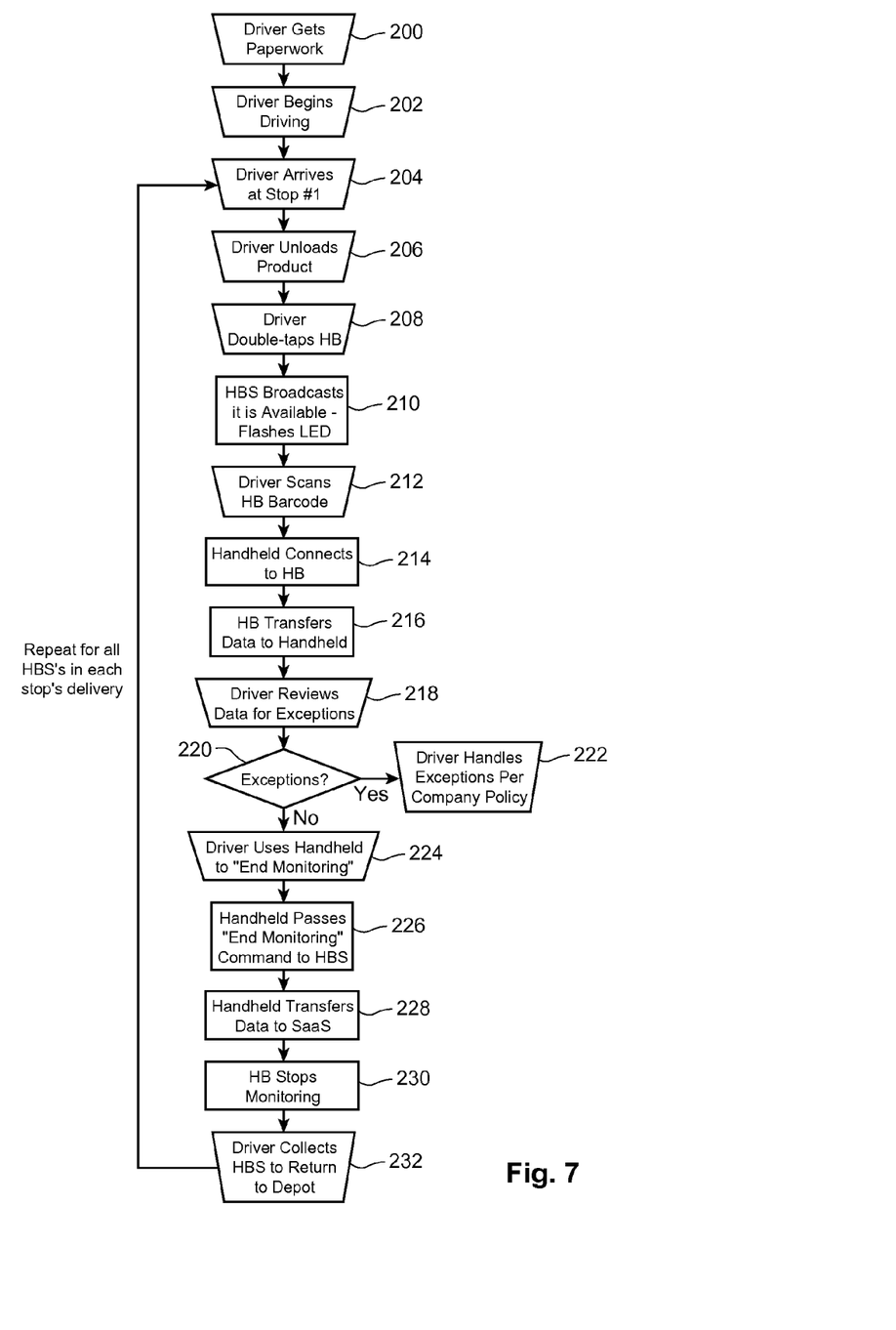
FIG. 7 is a flow diagram describing a method of operating a sensing device during transportation.
Figure 8:
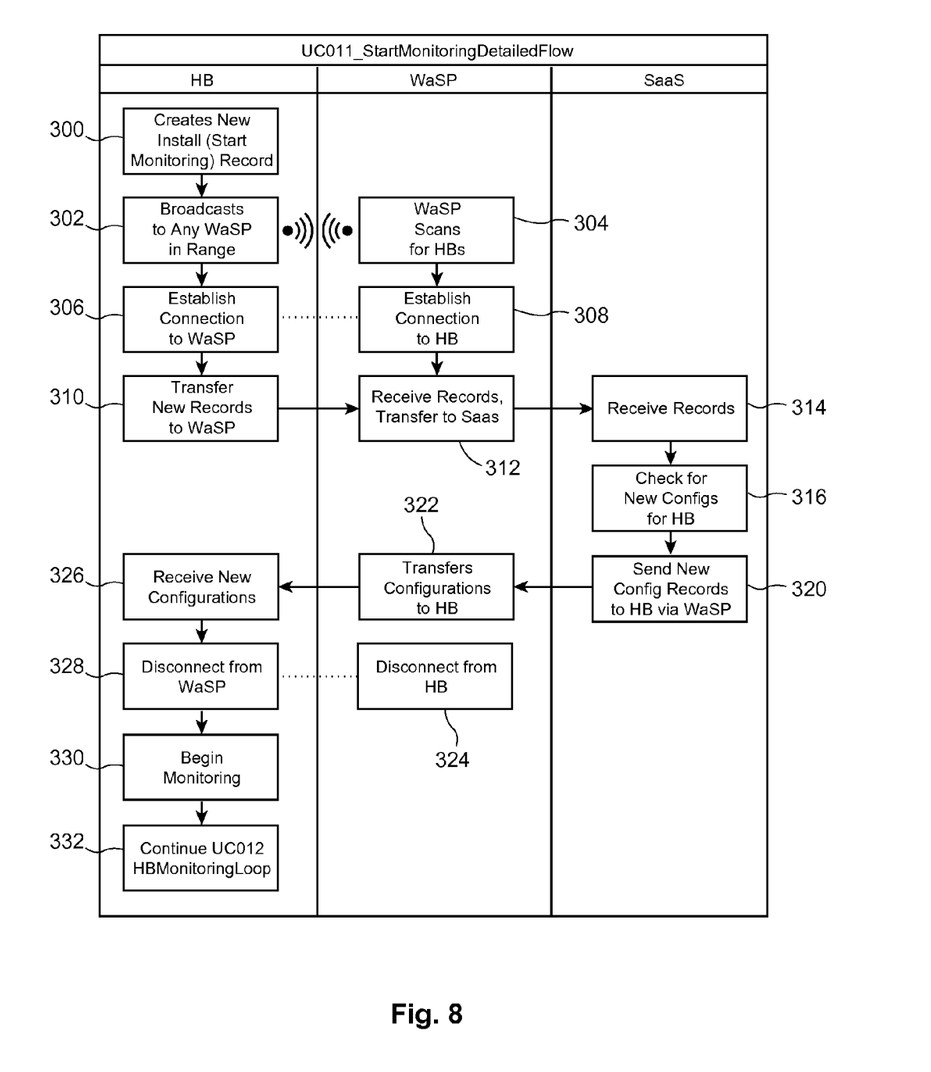
FIG. 8 is a flow diagram describing a method of communicating between a sensing device and a gateway or access point.

FIG. 7 describes a method of monitoring perishables being transported by vehicle. The driver will generally start by doing paperwork 200 and will begin driving 202. The driver will stop at a location 204 and load or unload some product 206. At this time, the driver will activate 208 the sensing device by double tapping the sensing device. If a server is available to receive information, the status display interface will indicate the presence of a connection 210, for example, by flashing the display lights. The driver will scan 212 the bar code 54 (FIG. 4) of the sensing device using a hand-held device 52 (FIG. 4). The sensing device will transfer data 216 to the hand-held device which may act as a gateway or access point. The driver reviews 218 data exceptions 220 and if there are exceptions, the driver will handle them 222 in accordance with the company's policy. The driver uses the hand-held device to end the monitoring period 224 by passing an end monitoring command 226 to the sensing device. The handheld device 228 will transfer the data collected from the sensing device to a separate location, such as a server or other location where the records are stored and in which configuration records may be stored, such as shown in FIG. 8. After the data is transferred to the separate location, the sensing device will note the trip end at 230 and the driver will collect the sensing device to return it to the depot 232 after the trip and event, the sensing device will continue sensing and recording. The steps 204 through 230 will be repeated for each sensing device in each stop's delivery.

In this sense monitoring conditions during a trip means collecting, recording or transmitting data during a time period of interest such as a time period between a shipping and a receiving location or a segment of a larger trip. The main aspect is that the time period of interest represents a period of time when the sensing device is active and recording data and the data is identified by a starting and ending event.

FIG. 8 is a flow chart showing a method of communication between a sensing device 20 (FIG. 1), a gateway or access point such as a hand-held device 52 (FIG. 4) and a separate processing location. The separate processing location may be a physical processor or a virtual processor which operates on a network of computers known as a cloud. In some embodiments, gateway or access point may communicate with the servers connected over the internet. For example, the separate processing location may be a server which is accessible through the internet or may be part of the gateway or access point. The physical attributes of the separate processing location are unimportant so long as the separate processing location allows for the storage of configuration records and stored condition data received by one or more sensing devices. The separate processing location may be denoted as software as a service, since it allows users of the sensing devices to track information about conditions detected by the sensors and allows the users to change the configuration of the sensing devices. Although the gateway or access point is described as a hand-held device, other devices can be used so long as those devices can communicate between the sensing device and the separate processing location. In some cases, the gateway or access point may also include the functionality of the separate processing location by including software to receive records and update configuration records. In other words, the gateway or access point may also be the processing location.

The separate processing location allows for robust reports to be made available online. The online reports may be made available so that owners can track inventory and the conditions of inventory during transportation and track the inventory when it is in storage. The various reports can be used to track system failures and to identify problems, such as drivers who are frequently careless with perishable products or to identify cooling systems which are defective. The storage of temperature information also ensures that records can be kept in compliance with food safety regulations. The data stored at the separate processing location can be accessed by a user through any communication device, for example through the internet or through a hand-held device.

As shown in FIG. 8, the sensing device will start monitoring 300. The sensing device broadcasts 302 to any gateway or access point in range and the gateway or access point 304 scans for sensing devices. A two-way connection is established from the sensing device to the gateway or access point 306 and from the gateway or access point to the sensing device 308. The stored condition data on the sensing device is transferred 310 from the sensing device and received 312 by the gateway or access point, where the stored condition data is transferred immediately or at a later time to the separate processing location. The separate processing location receives the stored condition data 314. The separate processing location checks 316 for new configuration records. The configuration records may be changed, for example, during the initialization of the sensing device or when the sensing device is being changed for a different operation. For example, if the sensing device was being used on a pallet with perishable products and the sensing device has now arrived at a store location where it will be used in a display cooler, the sensing device may require new configuration settings to adapt to the new environment. Similarly, if the perishable products being monitored are different, different condition sensing settings may be required. Any new configuration records will be transferred to the sensing device through the gateway or access point 322, and the configuration records will be received 326 by the sensing device. The gateway or access point and the sensing device disconnect 324, 328 from each other and the sensing device will begin monitoring 330. The sensing device will begin monitoring 332, for example, in accordance with the method described in FIG. 9.

FIG. 9 is an embodiment of a method of monitoring using the sensing device 20 (FIG. 1). The sensing device monitors temperature 400 in an environment. If a change 402 in temperature or time occurs which is a change that falls within the configuration records 404, then an event is triggered 406 and the event is stored 408. Storing the event may include storing one or more conditions in the environment, including temperature or time. The sensing device is then configured to be in broadcast mode 410, meaning that the sensing device will connect to a gateway or access point if one comes into range. The broadcast mode on the sensing device will remain active until it is switched off by the gateway or access point after communication between them has been completed.

The motion sensor in the sensing device is monitored 412. If a motion 414 is detected by the motion sensor which is a change that falls within the configuration records 416, then an event is triggered 418 and the conditions relating to the event is stored 420. The sensing device is then configured to be in broadcast mode 422. The motion sensor may be a gyroscope, compass or accelerometer and thereby detects an interruption in the normal operation of the sensing device.

When the sensing device detects a gateway or access point, such as a Bluetooth enabled hand-held device, is in range 424 and the broadcast is set to true 426, then if a connection is requested by the hand-held device 428 then the connection process 430 is started, such as is described in reference to FIG. 8.

An event detected by the motion sensor may be caused by the presence of any one of a number of triggers. For example, the sensing device may be responsive to a person rotating the device 180-degrees clockwise followed by a rotation of 180-degrees counterclockwise. Other types of motions can be used to trigger an event. The precise motion induced by the user is unimportant so long as it is difficult for that motion to be triggered accidentally and the user is easily able to cause that motion to occur. The motion triggered by the user may signal the beginning or end of a trip. After the trip has begun, any event recorded by the sensing device will be transmitted to a gateway or access point when the gateway or access point is in range. After the event has been communicated, the sensing device may become inactive for power savings.

If the sensing device is on a freezer door, opening the freezer door may trigger the current temperature to be recorded. Furthermore, opening the freezer door may also cause the sensing device to take more frequent readings after the door is opened to ensure that the temperature does not increase due to the door not fully closing.

If the sensing device is placed on a roll-door, the detection of an orientation change of 90 degrees rotation may trigger a door open event. The detection of an orientation change of −90 degrees would trigger a door close event. Similarly, if the sensing device is placed on a hinged door, an acceleration in one direction may cause a door open event, whereas acceleration in the opposite direction may cause a door close event. The door opening event may trigger the communication system of the sensing device to become active so that it can communicate with a gateway or access point at the unloading location and the door close event can act to cause the communication system of the sensing device to become inactive.

If the sensing device is placed on a pallet, the detection of acceleration against gravity followed by a period of vibration, followed by a period of no acceleration can trigger the start of an event. Similarly, the detection of acceleration in the downward direction, followed by a period of vibration and followed by a period of no acceleration may trigger an end event.

The sensing device may also be used to track events such as a break-in to a trailer or cooler.

The sensing device 20 (FIG. 1) thereby may create a full history of the product temperature including precisely at what time an exception occurred and the severity of the exception. This allows the owner of perishable goods to ensure the goods were kept in proper conditions in environments such as a cargo container, a dock, a trailer, a walk-in freezer or refrigerator, a display case, a meat display, deli case, dairy cases or other any locations so that a tamper-proof audit of the cold chain of the system is preserved.

The sensing device can be placed in a variety of locations in order to track the environment surrounding the perishable goods. The sensing device may be placed inside a product box or pallet where it may continuously monitor temperatures and exceptions from loading through unloading.

At the conclusion of a trip, a driver or receiver is able to review condition data for any exceptions that occurred since packing and this data may be automatically downloaded for reporting and analysis. The sensing device may then be re-used for another trip. The sensing device can be cleaned before re-use depending on how the sensing device is to be re-used.

The use of the system removes the need for manual recording of temperatures and ensures that temperature exceptions can be caught. The temperature sensors also ensure compliance with food safety regulations.

As described in FIGS. 8 and 9, the sensing device 20 may be connected to a gateway or access point. The gateway or access point may be, for example, a hand-held device 52 (FIG. 4) such as a cellphone or user-specific device. A user-specific device may be a simple keychain sized device that is responsive to touch that includes a display screen. By tapping the user-specific device against a sensing device, the user-specific device will be able to display the condition data on the sensing device. The user-specific device may be touch activated in a similar manner to the sensing device 20 (FIG. 1). The gateway or access point may also be any Bluetooth™ Low Energy capable cellphone. Software, such as an App, may be installed on the cellphone to allow it to communicate with one or more sensing devices.

Figure 10:
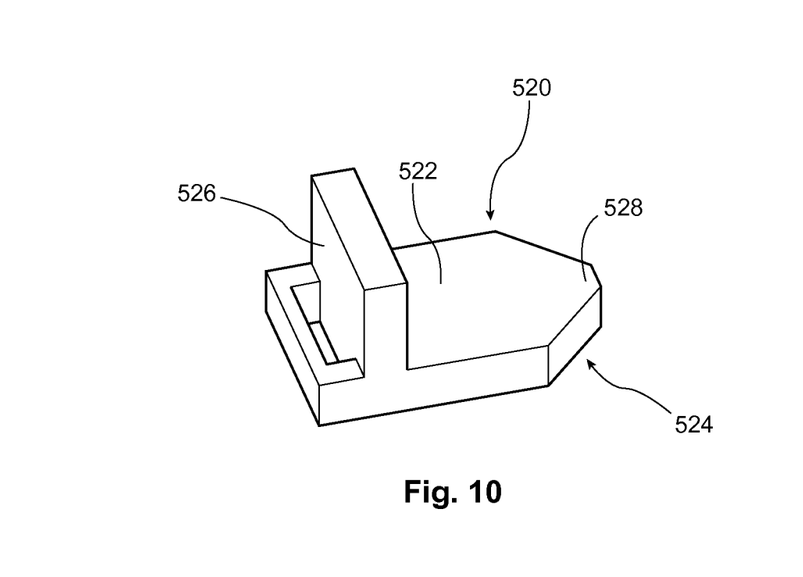
FIG. 10 is a perspective view of another embodiment of a sensing device.
Figure 11:
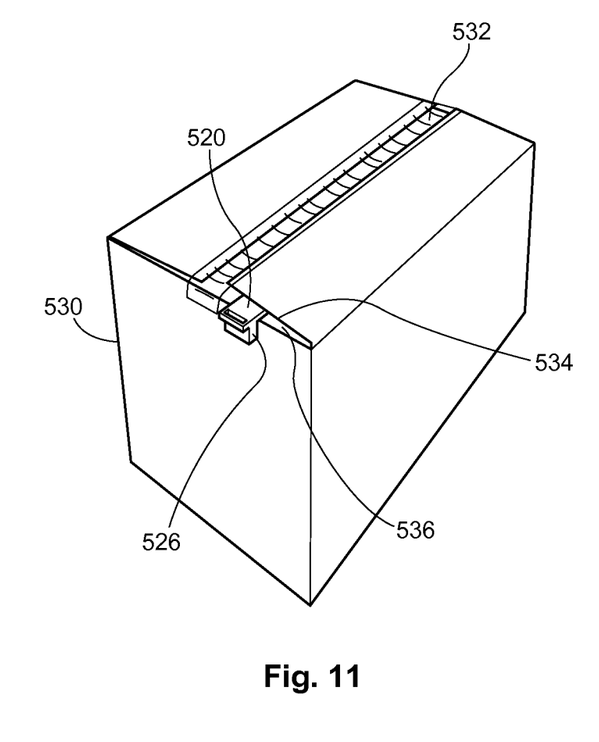
FIG. 11 is a perspective view of the embodiment of the sensing device of FIG. 10 inserted into a box.

FIGS. 10 and 11 show a sensing device 520 representing a specific configuration of the sensing device 20 of FIG. 1. Accordingly, the sensing device 520 may be made with a sealed body 522 suitable to contact food and which is cleanable for re-use. A low-energy wireless communicator 26 as shown in FIG. 1 is contained within said sealed body 522.

Preferably, the sensing device 520 contains a condition sensor 528 in the form of a temperature sensor. The temperature sensor 528 is enclosed within the sealed body 522 within a wedge end 524 of the sensing device 520. A block end 526 is situated on the sensing device 520 at the opposite end to the wedge end 524.

A processor 30 as shown in FIG. 1 is operatively connected to the condition sensor 528 and the wireless communicator 26 as shown in FIG. 1. An energy source 32 as shown in FIG. 1 is operatively connected to the processor 30 (FIG. 1) to supply power. Preferably, the sensing device 520 contains a memory 38 as shown in FIG. 1 which is operatively connected to the condition sensor 528 to store monitored conditions obtained by the condition sensor 528.

As shown in FIG. 11, the wedge end 524 of the sensing device 520 may be inserted between a top flap 534 and an inner flap 536 of a cardboard box 530 without otherwise disturbing the packaging or contents. For example, the sensing device 520 may be inserted into the box 530 without removing packing tape 532 or opening the flaps. The wedge end 524 containing the temperature sensor 528 is located in the portion of the sensing device 520 closest to the centre of the box 530 when the sensing device 520 is inserted into the box 530. The block end 526 of the sensing device 520 functions to prevent the device from being inserted entirely into the box 530 by an operator.

The use of the sensing device 520 to detect temperature allows for more accurate readings of the box contents' temperature. The top flap 534 acts as an insulation layer when the wedge end 524 is inserted into the box 530 to reduce erroneous measurements caused by ambient air fluctuations in the vicinity of the box 530. The placement of the sensing device 520 directly into packaging allows the temperature of the box contents to be measured more accurately without the need to open the box. The sensing device 520 is easily inserted, readily visible and may be quickly removed after a reading is taken.

In circumstances where the package is not owned by the shipper, or where disturbance or destruction of the outer packaging is prohibited or otherwise desirable to be avoided, the shipper or other interested party may monitor the contents of the box 530 without having to open it or break the seal.

While reference has been made to various preferred embodiments of the invention other variations, implementations, modifications, alterations and embodiments are comprehended by the broad scope of the appended claims. Some of these have been discussed in detail in this specification and others will be apparent to those skilled in the art. Those of ordinary skill in the art having access to the teachings herein will recognize these additional variations, implementations, modifications, alterations and embodiments, all of which are within the scope of the present invention, which invention is limited only by the appended claims.

The invention claimed is:

1. A sensing device for monitoring conditions in a local environment containing perishable goods and wirelessly communicating said monitored conditions, the sensing device comprising:
a sealed body comprised of a non-porous, water-proof material suitable to contact food and which is cleanable for re-use;
a low-energy wireless communicator contained within said sealed body;
a condition sensor contained within said sealed body;
a processor operatively connected to the condition sensor and the wireless communicator, the processor contained within said sealed body;
an energy source operatively connected to the processor to supply power, said energy source being contained within said sealed body;
a motion sensor operatively connected to the processor, for detecting motion of said sealed body, to act as a switch for said processor, said motion sensor being contained within said sealed body;
wherein said processor is switched on or off in response to the motion sensor detecting a pattern of motion induced on the device by a user;
wherein the motion induced by the user comprises rotating said sensing device in one direction by a predetermined degree, followed by rotating said sensing device in the opposite direction by said predetermined degree; and
wherein said sensing device may be placed in contact with perishable food products to monitor conditions affecting said perishable food products and communicate the monitored conditions by means of said wireless communicator.

2. The sensing device of claim 1 in which the sensing device further comprises a memory operatively connected to the condition sensor to store monitored conditions obtained by the condition sensor, the memory contained in said sealed body.

3. The sensing device of claim 1 further comprising a status display interface on said sealed body and operatively connected to the processor which indicates a current status of the sensing device.

4. The sensing device of claim 2 in which the low-energy wireless communicator further comprises a low-energy protocol radio module.

5. The sensing device of claim 1 in which the energy source is a battery.

6. The sensing device of claim 5 in which the battery is a lithium battery.

7. The sensing device of claim 1 in which the sensing device is activated by motion detected by the motion sensor.

8. The sensing device of claim 1 in which sensing device is a temperature sensing device and the condition sensor is a temperature sensor.

9. The sensing device of claim 8 in which the processor is adapted to cause the temperature sensor to detect a temperature in an environment in response to motion of said sealed body being detected by the motion sensor.

10. The sensing device of claim 4 in which both the memory and the processor are integrated into an internal processor of the radio module.

11. The sensing device of claim 1 in which the sealed body is comprised of a food-grade material and is configured to be sanitized.

12. A method of monitoring a condition of perishable food products using a sensing device, the sensing device comprising a sealed body comprised of a non-porous, waterproof material suitable to contact food and which is cleanable for re-use, a low-energy wireless communicator contained within said sealed body, a condition sensor contained within said sealed body, a processor operatively connected to the condition sensor and the wireless communicator, the processor contained within said sealed body, said processor is switched on or off in response to the motion sensor detecting a pattern of motion induced on the device by a user; an energy source operatively connected to the processor to supply power, said energy source being contained within said sealed body, a motion sensor operatively connected to the processor, for detecting motion of said sealed body, said motion sensor being contained within said sealed body; the method comprising:
- providing a sensing device which is placed in an environment containing the perishable food products;
- in which the sensing device is activated by inducing motion to be detected by the motion sensor;
- wherein the motion induced by the user comprises rotating said sensing device in one direction by a predetermined degree, followed by rotating said sensing device in the opposite direction by said predetermined degree;
- detecting a condition in the environment using the condition sensor;
- storing the detected condition in the environment on the sensing device in the form of stored condition data; and
- transmitting the stored condition data to a receiver using the low-energy wireless communicator.

13. The method of claim 12 in which the environment is one of a walk-in freezer or refrigerator, a display case, a warehouse and a vehicle cargo area.

14. The method of claim 12 in which all of the steps of detecting the condition in the environment, storing the detected condition and transmitting the stored condition data are done in real-time.

15. The method of claim 14 in which the step of transmitting the stored condition data to a receiver further comprising uploading the stored condition data to a server.

16. The method of claim 12 in which the steps of detecting the condition in the environment and storing the detected condition are repeated multiple times before the step of transmitting the stored condition data occurs.

17. The method of claim 12 in which the processor stores a configuration record correlating threshold conditions to an occurrence of a plurality of events, and the method further comprises monitoring at least one of:
- the condition in the environment using the condition sensor; and
- motion of the sealed body using the motion sensor; and
- recording the occurrence of an event when the at least one of the condition in the environment and the motion detected by the motion sensor correlates to an event in the plurality of events.

18. The method of claim 12 in which the step of detecting the condition in the environment using the temperature sensor is triggered after motion is detected by the motion sensor.

19. The method of claim 12 in which the step of detecting the condition in the environment is triggered by the processor at set intervals.

20. A system for monitoring a condition of perishable food products, comprising:
- at least one sensing device, comprising:
- a sealed body comprised of a non-porous, water-proof material suitable to contact food and which is cleanable for re-use;
- a low-energy wireless communicator contained within said sealed body; a condition sensor contained within said sealed body; a processor operatively connected to the condition sensor and the wireless communicator, the processor contained within said sealed body;
- an energy source operatively connected to the processor to supply power, said energy source being contained within said sealed body;
- a motion sensor operatively connected to the processor for detecting motion of said sealed body, to act as a switch for said processor, said motion sensor being contained within said sealed body;
- said processor is switched on or off in response to the motion sensor detecting a pattern of motion induced on the device by a user;
- wherein the motion induced by the user comprises rotating said sensing device in one direction by a predetermined degree, followed by rotating said sensing device in the opposite direction by said predetermined degree; and
- a hand-held mobile device having a wireless communicator which communicates with the low-energy wireless communicator of the sensing device.

21. The system of claim 20 in which the low-energy wireless communicator is a low-energy protocol radio module and the wireless communicator of the hand-held mobile device uses a low-energy protocol.

22. The system of claim 20 in which the system further comprises at least two sensing devices and in which the at least two sensing devices are configured to communicate with each other.

23. The system of claim 20 in which the sensing device is a temperature sensing device and the condition sensor is a temperature sensor.

24. The system of claim 20 in which the motion sensor is an accelerometer.

25. The system of claim 20 in which the energy source is a lithium battery.

26. A sensing device for monitoring conditions in a local environment containing perishable goods and wirelessly communicating said monitored conditions, the sensing device comprising:
- a sealed body comprised of a non-porous, water-proof material suitable to contact food and which is cleanable for re-use, the sealed body having a wedge end;
- a low-energy wireless communicator contained within said sealed body; a condition sensor contained within said sealed body and situated within the wedge end of the sealed body;
- a processor operatively connected to the condition sensor and the wireless communicator, the processor contained within said sealed body;
- a motion sensor operatively connected to the processor for detecting motion of said sealed body, to act as a switch for said processor;
- said processor is switched on or off in response to the motion sensor detecting a pattern of motion induced on the device by a user;
- wherein the motion induced by the user comprises rotating said sensing device in one direction by a predetermined degree, followed by rotating said sensing device in the opposite direction by said predetermined degree;
- an energy source operatively connected to the processor to supply power, said energy source being contained within said sealed body;
- wherein the wedge end of the sensing device may be placed in the local environment containing perishable food products to monitor conditions affecting said perishable food products and communicate the monitored conditions by means of said wireless communicator.

27. The sensing device of claim 26 further comprising a block end forming part of the sealed body opposite to the wedge end.

28. The sensing device of claim 26 in which the condition sensor further comprises a temperature sensor.

29. The sensing device of claim 26 further comprising a motion sensor operatively connected to the processor, for detecting motion of said sealed body, to act as a switch for said processor.

30. The sensing device of claim 27 further comprising a motion sensor operatively connected to the processor, for detecting motion of said sealed body, to act as a switch for said processor.

31. The sensing device of claim 28 further comprising a motion sensor operatively connected to the processor, for detecting motion of said sealed body, to act as a switch for said processor.

32. The sensing device of claim 1, wherein said processor is switched on or off in response to the motion sensor detecting a pattern of one or more taps by a user.

33. The sensing device of claim 1, wherein said predetermined degree is at least 180°.

34. The sensing device of claim 1, wherein said sealed body is formed as a seamless piece of said material.

35. The sensing device of claim 1, wherein said sealed body is free from crevices interfering with cleaning said sealed body for re-use.

* * * * *

UNITED STATES PATENT AND TRADEMARK OFFICE
CERTIFICATE OF CORRECTION

PATENT NO. : 9,712,893 B2
APPLICATION NO. : 14/255640
DATED : July 18, 2017
INVENTOR(S) : Colin Warkentin et al.

It is certified that error appears in the above-identified patent and that said Letters Patent is hereby corrected as shown below:

In the Claims

Claim 4, Column 14, Lines 36-38, replace "The sensing device of claim 2 in which the low-energy wireless communicator further comprises a low-energy protocol radio module." with -- The sensing device of claim 2 in which the low-energy wireless communicator further comprises a radio module. --.

Claim 8, Column 14, Lines 45-47, replace "The sensing device of claim 1 in which sensing device is a temperature sensing device and the condition sensor is a temperature sensor." with -- The sensing device of claim 1 in which the sensing device is a temperature sensing device and the condition sensor is a temperature sensor. --.

Claim 21, Column 16, Lines 17-20, replace "The system of claim 20 in which the low-energy wireless communicator is a low-energy protocol radio module and the wireless communicator of the hand-held mobile device uses a low-energy protocol." with -- The system of claim 20 in which the low-energy wireless communicator is a radio module. --.

Signed and Sealed this
Nineteenth Day of March, 2019

Andrei Iancu
*Director of the United States Patent and Trademark Office*